United States Patent
Bar-Zion et al.

(10) Patent No.: US 10,610,193 B2
(45) Date of Patent: Apr. 7, 2020

(54) CONTINUOUS ULTRASONIC MONITORING

(71) Applicant: Hemonitor Medical Ltd., Haifa (IL)

(72) Inventors: Avinoam Bar-Zion, Haifa (IL); Tom Mayblum, Tel-Aviv (IL); Samer Toume, Haifa (IL)

(73) Assignee: Hemonitor Medical Ltd., Haifa (IL)

(*) Notice: Subject to any disclaimer, the term of this patent is extended or adjusted under 35 U.S.C. 154(b) by 305 days.

(21) Appl. No.: 15/390,792

(22) Filed: Dec. 27, 2016

(65) Prior Publication Data

US 2017/0105700 A1    Apr. 20, 2017

Related U.S. Application Data

(63) Continuation-in-part of application No. PCT/IL2016/050664, filed on Jun. 22, 2016.

(60) Provisional application No. 62/183,278, filed on Jun. 23, 2015.

(51) Int. Cl.
 *A61B 8/00* (2006.01)
 *A61B 8/06* (2006.01)
 *A61B 8/08* (2006.01)

(52) U.S. Cl.
 CPC ........... *A61B 8/065* (2013.01); *A61B 8/06* (2013.01); *A61B 8/0891* (2013.01); *A61B 8/4236* (2013.01); *A61B 8/4272* (2013.01); *A61B 8/4427* (2013.01); *A61B 8/4483* (2013.01); *A61B 8/488* (2013.01); *A61B 8/5223* (2013.01); *A61B 8/54* (2013.01)

(58) Field of Classification Search
 None
 See application file for complete search history.

(56) References Cited

U.S. PATENT DOCUMENTS

| | | | |
|---|---|---|---|
| 5,487,388 A | 1/1996 | Rello et al. | |
| 5,598,845 A | 2/1997 | Chandraratna et al. | |
| 5,722,411 A * | 3/1998 | Suzuki | A61N 7/02 600/439 |
| 5,844,140 A * | 12/1998 | Seale | A61B 8/08 73/633 |

(Continued)

FOREIGN PATENT DOCUMENTS

| | | |
|---|---|---|
| WO | WO2012/101511 | 8/2012 |
| WO | WO 2016/207889 | 12/2016 |

OTHER PUBLICATIONS

International Search Report for PCT Application No. PCT/IL2016/050664 dated Sep. 29, 2016.

(Continued)

*Primary Examiner* — Joanne M Hoffman (57) ABSTRACT

A system for continuous ultrasonic monitoring includes an ultrasound transducer. The ultrasound transducer includes an array of ultrasonic transducer elements. The ultrasonic transducer elements are operable to steer and focus an ultrasound beam to a selectable location and to receive an ultrasound signal from the selectable location. A holder is provided for holding the ultrasound transducer, the holder being attachable to a skin surface of a patient. A controller is configured to repeatedly steer and focus the ultrasound beam to identify a target section of an object inside the body of the patient and to acquire an ultrasound image such that the target section is maintained within the acquired ultrasound image.

20 Claims, 6 Drawing Sheets

(56) References Cited

U.S. PATENT DOCUMENTS

| | | | | |
|---|---|---|---|---|
| 6,059,727 | A * | 5/2000 | Fowlkes | A61B 8/08 |
| | | | | 128/916 |
| 6,131,459 | A * | 10/2000 | Seale | A61B 8/4461 |
| | | | | 310/90.5 |
| 6,425,865 | B1 * | 7/2002 | Salcudean | A61B 8/0875 |
| | | | | 600/111 |
| 6,599,256 | B1 * | 7/2003 | Acker | A61D 1/06 |
| | | | | 600/439 |
| 6,682,483 | B1 * | 1/2004 | Abend | G01S 7/52026 |
| | | | | 128/916 |
| 6,719,698 | B2 | 4/2004 | Manor et al. | |
| 8,235,903 | B2 * | 8/2012 | Abraham | A61B 5/076 |
| | | | | 600/439 |
| 2004/0059220 | A1 * | 3/2004 | Mourad | A61B 5/0048 |
| | | | | 600/442 |
| 2011/0230764 | A1 * | 9/2011 | Baba | A61B 8/06 |
| | | | | 600/454 |
| 2013/0165783 | A1 | 6/2013 | Kim et al. | |
| 2013/0204127 | A1 * | 8/2013 | Hoogi | A61B 8/481 |
| | | | | 600/431 |
| 2014/0107435 | A1 * | 4/2014 | Sharf | A61B 8/06 |
| | | | | 600/301 |
| 2014/0114194 | A1 * | 4/2014 | Kanayama | A61B 8/5215 |
| | | | | 600/459 |
| 2014/0378835 | A1 * | 12/2014 | Satoh | A61B 8/06 |
| | | | | 600/441 |
| 2019/0046158 | A1 * | 2/2019 | Kroon | A61B 8/08 |

OTHER PUBLICATIONS

International Search Report and the Written Opinion dated Sep. 29, 2016 From the International Searching Authority Re. Application No. PCT/IL2016/050664. (11 Pages).

International Search Report and the Written Opinion dated Apr. 15, 2018 From the International Searching Authority Re. Application No. PCT/IB2017/057932. (12 Pages).

* cited by examiner

CONTINUOUS ULTRASONIC MONITORING

CROSS REFERENCE TO RELATED APPLICATIONS

The present invention is a continuation-in-part of International Patent Application No. PCT/IL2016/050664 with an international filing date of Jun. 22, 2016, which in turn claims the priority benefit of U.S. provisional patent application No. 62/183,278, filed on Jun. 23, 2015, both of which are incorporated in their entirety herein by reference.

FIELD OF THE INVENTION

The present invention relates to ultrasonic monitoring. More particularly, the present invention relates to continuous ultrasonic monitoring.

BACKGROUND OF THE INVENTION

Fluid management is typically required for all intensive care unit (ICU) patients. In the case of critically ill patients, fluid management is an important and difficult issue. Fluid resuscitation is an initial therapeutic intervention with patients after suffering a trauma, or when symptoms of hypotension, evidence of poor organ/tissue perfusion, or other significant hemodynamic challenges are present. Fluid resuscitation refers to the medical practice of replenishing body fluids lost through perspiration, bleeding, fluid shifts, or other pathological processes. The replenishing may include introduction of fluids orally, intravenously, or otherwise.

In some cases, suboptimal administration of fluid resuscitation may lead to an increase in morbidity and mortality in critically ill patients. Therefore, fluid management, in which fluid resuscitation is coordinated with hemodynamic monitoring, is an important component of the treatment of patients requiring fluid resuscitation. Various types of hemodynamic monitors may provide physicians with measurements of various hemodynamic parameters. Such parameters may include stroke volume (the volume of blood that is pumped from the left ventricle during each heartbeat), heart rate, cardiac output, respiration rate, or other relevant hemodynamic parameters. Knowledge of the values of such parameters may assist a physician in determining whether or not fluid resuscitation is necessary, and if it is, what quantity of fluid is to be administered.

The hemodynamic monitors that are most widely used are invasive devices. For example, an invasive device may include one or more catheters or sensors that are inserted into the patient's blood vessels.

Ultrasound imaging is widely used as a tool for medical diagnostics. Ultrasound imaging may provide high-resolution images of internal organs and biological structures deep inside the body, as well as functional information, e.g., with regard to cardiac function and blood flow. A typical ultrasound transducer includes an array of elements that emit and receive ultrasonic waves. When operated in brightness mode (B-mode), an ultrasound system may generate real time two-dimensional images based on the received waves. When operated in Doppler mode, the ultrasound system may provide measurements of the velocities of blood and tissue. Doppler ultrasound may be used to estimate blood velocity by transmitting streams of high-frequency sound waves and analyzing the signals reflected from circulating red blood cells. The local velocity profile is derived from measured changes in the phase of a received signal. Doppler scans may be used in the diagnosis of such conditions as heart valve defects, congenital heart disease, artery occlusions, and aneurysms.

SUMMARY OF THE INVENTION

There is thus provided, in accordance with an embodiment of the present invention, a system for continuous ultrasonic monitoring, the system including: an ultrasound transducer, the ultrasound transducer including an array of ultrasonic transducer elements, the ultrasonic transducer elements being operable to steer and focus an ultrasound beam to a selectable location and to receive an ultrasound signal from the selectable location; a holder for holding the ultrasound transducer, the holder being attachable to a skin surface of a patient; and a controller that is configured to repeatedly steer and focus the ultrasound beam to identify a target section of an object inside the body of the patient and to acquire an ultrasound image such that the target section is maintained within the acquired ultrasound image.

Furthermore, in accordance with an embodiment of the present invention, the controller is configured to operate the ultrasound transducer in Doppler mode.

Furthermore, in accordance with an embodiment of the present invention, the target section includes a section of a blood vessel, the controller being configured to operate the ultrasound transducer in Doppler mode to acquire a measurement of a flow rate of blood in the target section and to calculate a value of a hemodynamic parameter using the measured flow rate.

Furthermore, in accordance with an embodiment of the present invention, the target section includes a section of the ascending aorta, the aortic arch, or the descending aorta.

Furthermore, in accordance with an embodiment of the present invention, the hemodynamic parameter is selected from a group of hemodynamic parameters consisting of stroke volume, cardiac output, stroke volume variation and systemic vascular resistance.

Furthermore, in accordance with an embodiment of the present invention, the holder includes a patch that includes one or a plurality of adhesive surfaces for attaching the holder to the skin surface.

Furthermore, in accordance with an embodiment of the present invention, the one or a plurality of adhesive surfaces includes an adhesive rim at a periphery of the patch.

Furthermore, in accordance with an embodiment of the present invention, the holder includes a retaining structure for retaining an ultrasound coupling material between the plurality of ultrasonic transducers and the skin surface.

Furthermore, in accordance with an embodiment of the present invention, the ultrasound coupling material includes a gel or a grease.

Furthermore, in accordance with an embodiment of the present invention, the holder includes a holding structure for holding the ultrasound transducer, the holding structure being configured to engage corresponding structure of the ultrasound transducer.

Furthermore, in accordance with an embodiment of the present invention, the controller is configured to repeatedly steer and focus the ultrasound beam to identify the target section by operating the ultrasound transducer in B-mode to acquire an image of a region of the patient that includes the target section.

Furthermore, in accordance with an embodiment of the present invention, the controller is configured to continuously alternate operation of the ultrasound transducer between B-mode and Doppler mode.

Furthermore, in accordance with an embodiment of the present invention, the holder is configured to be attached to the skin surface of the suprasternal notch or the upper abdomen of the patient.

Furthermore, in accordance with an embodiment of the present invention, the controller is configured to calculate an angle between an axis of the target section and a direction of the ultrasound beam.

Furthermore, in accordance with an embodiment of the present invention, the controller is configured to measure a diameter of the target section.

There is further provided, in accordance with an embodiment of the present invention, a method for automatic operation of a continuous ultrasonic monitoring system, the method including: with an ultrasound transducer of the system held to a skin surface of a patient and positioned to steer and focus an ultrasound beam to a location within a body of the patient, the location including a target section, and to receive an ultrasound signal from the location, automatically operating the ultrasound transducer by a controller of the system to repeatedly steer and focus the ultrasound beam to identify the target section and to acquire an ultrasound image such that the target section is maintained within the acquired ultrasound image.

Furthermore, in accordance with an embodiment of the present invention, automatically operating the ultrasound transducer includes operating the ultrasound transducer in Doppler mode.

Furthermore, in accordance with an embodiment of the present invention, automatically operating the ultrasound transducer includes operating the ultrasound transducer alternately in B-mode and Doppler mode.

Furthermore, in accordance with an embodiment of the present invention, automatically operating the ultrasound transducer includes automatically operating the ultrasound transducer to steer and focus a Doppler measurement beam on the target section.

Furthermore, in accordance with an embodiment of the present invention, automatically operating the ultrasound transducer includes modifying a field of view of the ultrasound transducer to maintain the target section within the acquired ultrasound image.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

Some embodiments of the invention may include an article such as a computer or processor readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein.

In accordance with an embodiment of the present invention, a continuous ultrasonic monitoring system is provided to continuously monitor an anatomical structure by maintaining an object within the body of a patient within an ultrasound image. For example, the object may include an anatomical structure such as an organ, blood vessel, or tumor, or a foreign object (e.g., an implanted or ingested object, or an object that is introduced into the body as a result of injury). The system includes an ultrasound measurement unit. The ultrasound measurement unit is configured to attach to the body of a patient, to transmit ultrasound pulses into the patient's body, and to receive ultrasound signals that are reflected from internal structures in the patient's body.

In particular, the ultrasound monitoring system may be utilized to continuously and non-invasively monitor stroke volume, cardiac output (blood volume per unit time, e.g., calculated by multiplying stroke volume by heart rate), stroke volume variations, systemic vascular resistance, or another hemodynamic parameter.

The ultrasound measurement unit includes an ultrasound transducer that includes an array of ultrasonic transducer elements. The system includes a beam former that may introduce phase delays between the signals that are transmitted or received by each of the ultrasonic transducer elements. The beam former may control the phases to do one or more of focus the transmitted ultrasonic beam in the plane of the array to a selectable distance from the ultrasound transducer, receive ultrasound signals from point at a selectable distance from the ultrasound transducer, to aim the ultrasound beam in a selectable direction in the plane of the array, to receive ultrasound from a selectable direction in the plane of the array, or to produce a plane wave. The ultrasonic transducer elements of the ultrasound transducer may be operated in an imaging mode (B-mode) to produce an image, or in Doppler mode to measure a velocity of a measured object or flow.

The ultrasound transducer may be attached to a part of the body of a patient so as to acquire measurements within a region of the patient's body. For example, the region may include the thoracic region or upper abdomen of the patient, or another region of the patient (e.g., the leg, neck, or another part of the body). For example, the ultrasound transducer may be attached to the suprasternal notch, upper abdomen, or elsewhere on the patient. The ultrasound transducer may be attached to the patient's body such that the ultrasonic transducer is aimed toward one or more major blood vessels, or another anatomical structure. For example, an ultrasound transducer that is attached to the suprasternal notch may be aimed toward the ascending aorta, the descending aorta or the aortic arch of the patient. An ultrasound transducer that is attached to the upper abdomen may be aimed toward the descending aorta of the patient. In some cases, the ultrasound transducer may have dimensions that are less than 3 centimeters. For example, a length or width of the ultrasound transducer may be in the range of 1 cm to 1.5 cm.

An adhesive patch may be provided to hold the ultrasound transducer to the patient's body. The adhesive patch may include a probe holder that includes a frame, receptacle, socket, or other structure for holding the ultrasound transducer. For example, one or both of the ultrasound transducer and the probe holder may include clips, latches, magnets, pins, or other structure that is configured to engage corresponding structure (e.g., tabs, loops, ferromagnetic plates, bores, sockets, or other corresponding structure) of the other.

The adhesive patch includes one or more adhesive surfaces. The adhesive surfaces are configured to adhere to the patient's skin when placed or pressed against the skin surface. For example, the adhesive surfaces may form an outer boundary of the adhesive patch, e.g., in the form of a circular, rectangular, or otherwise shaped ring. The size and shape of the adhesive surfaces may be configured to effectively hold the adhesive patch to a particular region of the patient's skin. For example, the size and shape may be configured to hold the adhesive patch to the patient's suprasternal notch or to the patient's upper abdomen.

Alternatively or in addition to an adhesive patch, the probe holder may be attached to the patient's body using suction, straps, clips, or otherwise.

The adhesive patch includes a structure for containing an acoustic coupling material between the ultrasound transducer and the patient's skin. For example, the acoustic coupling material may include an acoustic coupling gel, grease, or other material that may enable efficient propagation of ultrasound signals between the ultrasonic transducers and the skin surface. The structure for holding the acoustic coupling material may include walls to form a bath or chamber that may be fully or partially filled with the acoustic coupling material.

The system may be configured to operate the ultrasonic transducer elements to operate concurrently or alternately in B-mode and in Doppler mode. For example, Doppler and B-mode and measurements may be interleaved with instantaneous switching between Doppler and B-mode pulse sequences. During operation in B-mode, an ultrasound B-mode image of the interior of the patient may be acquired. The image may be expected to include an image of one or more sections of an internal object such as the patient's aorta. For example, when the ultrasound transducer is attached to the suprasternal notch, the image may include part of the ascending aorta or the aortic arch. When the ultrasound transducer is attached to the upper abdomen, the image may include part of the descending aorta.

One or more image processing techniques may be applied to the acquired image to automatically detect and identify one or more target sections. For example, automatic detection of the target section may be based on one or more of an expected size of the target section, a characteristic shape of the target section, a position of the target section relative to other identifiable anatomic features, or other detected or measured features. Various ultrasound imaging and display modes may be utilized, such as B-mode, motion mode (M-mode), color Doppler, spectral Doppler, or other modes.

For example, detection may be based on performing a template matching procedure. An acquired image may be compared to a bank of typical ultrasound images of the region that includes the target section. Correspondence of the acquired image with each image in the bank may be assessed by comparing the image correlation scores of the acquired image with different images in the image bank. Other techniques may be applied.

Upon identification in the image of the target section, one or more parameters of the target section may be derived from the image. For example, a diameter of the cross section of a target section of the aorta may be automatically measured from identified boundaries of the aorta. In some cases, at least an approximate orientation of the identified target section relative to the ultrasound transducer may be automatically determined, e.g., by comparison with images neighboring or other identified anatomical features, or by other characteristics (e.g., from analysis of blood flow within a target section of the aorta).

Continued operation in B-mode may be controlled such that the target section remains in subsequent acquired images. For example, an orientation of an imaged sector may be adjusted such that the target section remains at an approximately constant position within the acquired images.

When the ultrasonic transducer is operated in Doppler mode, the Doppler measurement ultrasound beam may be steered toward, focused on, or both the identified target section. For example, the ultrasound transducer may be operated to obtain a measurement of a velocity of the blood in an identified target section of a blood vessel such as the aorta. By alternating between operation of the ultrasound transducer in B-mode and operation in Doppler mode, the ultrasonic beam during operation in Doppler mode may be kept aimed at and focused on the target section. For example, the period of alternation may be sufficiently short such that typical anticipated body movements (e.g., breathing, voluntary movement of a limb, head, or other body part, or other relatively slow movements) do not significantly change the position of the ultrasound transducer relative to the target section. Alternatively or in addition, a sensor measurement may be used for gating the ultrasonic measurements in accordance with detected movements (e.g., heartbeat, breathing, or other cyclic motions).

For example, when the ultrasound transducer is operated in Doppler mode, ultrasound beam may be scanned over the identified target section. Thus, the velocity of the blood flow at different points on a cross section of the target section of the aorta may be measured. One or more of the measured blood flow velocity profile, measured dimensions (e.g., diameter or other dimension) of the target section, a measured heartbeat rate (e.g., measured using the ultrasound transducer or measured otherwise), or other measured quantities may be utilized to calculate a stroke volume, or one or more other hemodynamic parameters. In some cases, e.g., when the ultrasound transducer is placed at the suprasternal notch and the target section is the ascending aorta, the direction of the blood flow may be assumed to be approximately parallel to the direction of the ultrasound beam. For example, measurements may be limited to a plane (or spherical cap) that is approximately perpendicular to the ultrasound beam.

In some cases, e.g., when the ultrasound transducer is placed on the upper abdomen and the target section is the descending aorta, the measured blood flow profile may be utilized to calculate an angle between the direction of blood flow in the target section and the direction of the ultrasound beam. The calculated angle may be used in calculating the stroke volume.

A continuous ultrasonic monitoring system in accordance with an embodiment of the present invention may be advantageous over other techniques or devices for hemodynamic monitoring. A continuous ultrasonic monitoring system in accordance with an embodiment of the present invention enables continuous noninvasive hemodynamic monitoring. The continuous ultrasonic monitoring system may be prepared for operation and operated quickly and easily by a technician who lacks extensive medical training. Once the continuous ultrasonic monitoring system is prepared for use, the system may be left alone to continue monitoring, with no further attention or handling on the part of any personnel (or entail, at most, minimal adjustment).

For example, invasive hemodynamic monitors require insertion of a catheter into a blood vessel. Using an invasive monitor, requiring skill and time to insert the catheters and obtain the measurements, could entail delays that could lead to increased complications in treatment. Furthermore, the high cost per use of invasive hemodynamic monitors may limit the number of patients that may be monitored at the same time. Administering fluid treatment without hemodynamic monitoring, and thus without determining the responsiveness of a patient to treatment, could result in increased in morbidity, mortality, or a longer stay in a hospital.

Typical ultrasound systems may be utilized to estimate blood flow velocities by transmitting streams of high-frequency sound waves and analyzing the signals reflected from circulating red blood cells. Currently, most ultrasound Doppler techniques measure the component of blood velocity that is parallel to the direction of the beam. These one-dimensional measurements depend on the spatial angle between the transmitted beam and the direction of the flow. Development of vector Doppler methods that apply apodization may create a transverse modulation of the ultrasound beam, thus enabling the measurement of the flow velocity within an entire two-dimensional imaging plane. Extension of vector Doppler imaging to three dimensions entails using expensive two dimensional matrix transducers and high-end scanners. Current ultrasound imaging methodology requires manual handling, e.g., positioning and aiming, of the ultrasound probe. Thus, the use of ultrasound in fluid resuscitation management may be limited in a situation (e.g., an operating room or emergency room) where access to the patient is required from several directions, or where trained personnel are required for the performance of more urgent tasks.

Figure 1:
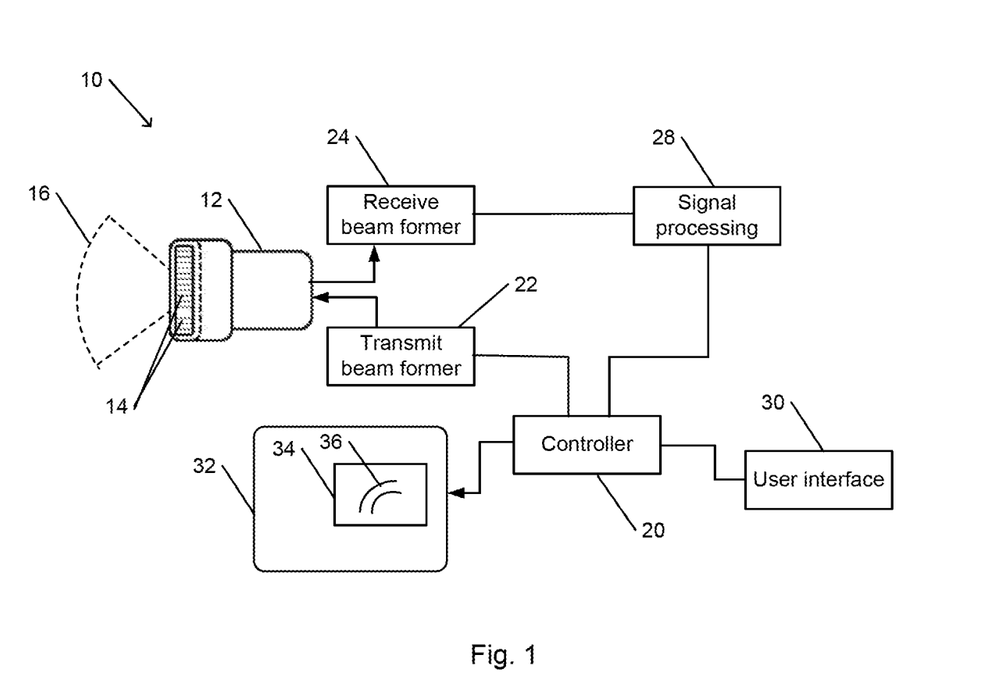
FIG. 1 shows a block diagram of a system for continuous ultrasonic monitoring, in accordance an embodiment of the present invention.

FIG. 1 shows a block diagram of a system for continuous ultrasonic monitoring, in accordance an embodiment of the present invention.

Continuous ultrasonic monitoring system 10 is configured to monitor one or more hemodynamic parameters of a patient. Ultrasound transducer 12 of continuous ultrasonic monitoring system 10 is configured to be attached to a surface of the skin of the patient.

Ultrasound transducer 12 includes an array of ultrasonic transducer elements 14. The array may be linear, curved, or two dimensional. Each ultrasonic transducer element 14 may include a piezoelectric transducer, a capacitive micromachined ultrasonic transducer (CMUT), or another suitable ultrasonic transducer element.

For example, the array of ultrasonic transducer elements 14 may be controlled to function as a phased array to produce or receive a steerable ultrasound signal. For example, the signal may be in the form of a pulsed ultrasound signal (e.g., equivalent to a series of continuous waves having a particular spectrum of wavelengths and phases). Ultrasound transducer 12 may be configured to generate ultrasound signals that may be transmitted to, and whose reflections may be received from, points within ultrasound field of view 16 of ultrasound transducer 12. Ultrasound field of view 16 represents a substantially planar range, whose thickness is much smaller than its other dimensions.

Controller 20 is configured to control operation of ultrasound transducer 12 and of associated electronics to as to obtain a desired measured result. For example, the measured result may include a B-mode image of ultrasound that is reflected from various structures within a patient's body, or a Doppler mode measurement of a velocity of an object or collection of objects (e.g., blood cells) within the patient's body.

Controller 20 may include a standalone unit that includes processing capability and is dedicated to operation of continuous ultrasonic monitoring system 10. Alternatively or in addition, controller 20 may include a software module, circuit board, or other software or hardware components that are incorporated within, connected to, or otherwise hosted by a general purpose computer.

A processor of controller 20 may be configured to operate in accordance with programmed instructions. For example, the programmed instructions may be stored in a memory or data storage device with which the processor is configured to communicate.

One or more of transmit beam former 22, receive beam former 24, and a digital processing unit may include a separate or distinguishable hardware component or circuitry within controller 20, a software module of programmed instructions for operation of a processor or processing unit of controller 20, or may represent a functionality of controller 20.

Transmit beam former 22 is configured to individually control transmission by each ultrasonic transducer element 14 so as to produce an ultrasonic beam with particular characteristics. The relative phases, amplitudes, and pulse shapes of ultrasound signals that are produced by each ultrasonic transducer element 14 may be controlled to form an ultrasonic beam having particular characteristics. For example, the beam may be aimed in a selectable direction within ultrasound field of view 16, or to modify ultrasound field of view 16 (e.g., rotate ultrasound field of view 16 or change the distance to the near and far boundaries of ultrasound field of view 16). Alternatively or in addition, the relative phases may be controlled to form a beam that is focused at a selectable distance from ultrasonic transducer elements 14 within ultrasound field of view 16. Ultrasonic transducer elements 14 may be controlled to form plane waves.

The transmitted signal may be reflected back toward ultrasonic transducer elements 14. For example, the signal may be reflected from blood cells in the aorta or another blood vessel, from walls of the aorta or another blood vessel, or from another structure, surface, or interface within the patient's body. Ultrasonic transducer elements 14 may detect the reflected signal.

Receive beam former 24 may be operated to receive signals from a selectable direction within ultrasound field of view 16. For example, receive beam former 24 may control synchronization of the signals that are received by each ultrasonic transducer element 14 so as to detect (e.g., reflected) ultrasound signals that originate from a selectable direction relative to ultrasound transducer 12. Similarly, receive beam former 24 may control synchronization of the signals that are received by each ultrasonic transducer element 14 so as to detect ultrasound signals that originate from a selectable distance from ultrasound transducer 12.

The received signals may be processed by signal processing unit 28. Signal processing unit 28 may perform one or more functions for extracting a desired measurement from the received signal.

For example, signal processing unit 28 may be configured to distinguish a received reflected ultrasound pulse from a carrier wave (e.g., demodulation) or background noise (e.g. filtering).

Signal processing unit 28 may be configured to determine an intensity or amplitude ("brightness") of an ultrasound pulse that is received at each point within ultrasound field of view 16. Thus, signal processing unit 28 may produce a B-mode image of structure within ultrasound field of view 16.

Signal processing unit 28 may be configured to operate in Doppler mode to calculate the phase shifts of consecutive ultrasound pulses that are reflected from a point or region within ultrasound field of view 16. These phase shifts may be analyzed to yield a component of velocity of the structure that reflected the pulses toward or away from ultrasound transducer 12. For example, if the structure includes blood cells, the measurement may yield a velocity of a component of the blood flow toward or away from ultrasound transducer 12.

A processing capability of controller 20 may analyze results from measurements using ultrasound transducer 12 to yield one or more hemodynamic parameters. For example, results of B-mode operation and Doppler mode operation may be utilized to calculate a stroke volume, or another hemodynamic parameter.

A user of continuous ultrasonic monitoring system 10 may operate controller 20 via user interface 30. For example, user interface 30 may include one or more screen controls or input devices (e.g., switches, pushbuttons, levers, dials, knobs, touch screens, pointing devices, keyboards, keypads, or other input devices) that enable a user to input one or more instructions to controller 20. For example, instructions may include an instruction to begin or stop operation, operating parameters, patient information, or other instructions.

Results of operation of continuous ultrasonic monitoring system 10 may be displayed on monitor 32. For example, alphanumeric characters may be displayed on monitor 32 to indicate the value of one or more hemodynamic parameters, such as stroke volume, heartbeat rate, or other hemodynamic parameters. For Monitor 32 may be operated to display warnings or notifications to a user, results of analysis (e.g., a stroke volume or other hemodynamic parameter), patient information, or other information.

Monitor 32 may display an ultrasound image 34. Ultrasound image 34 may include an image or one or more anatomical structures 36 (e.g., the aortic arch, descending aorta, heart, or other structure of interest). For example, ultrasound image 34 may include a B-mode image of anatomical features within ultrasound field of view 16. In some cases, a B-mode image may be modified to display additional information. For example, parts of ultrasound image may be color coded or otherwise modified to display velocity results of Doppler mode measurements, e.g., within images of the aorta, or where Doppler mode measurements were made.

Figure 2A:
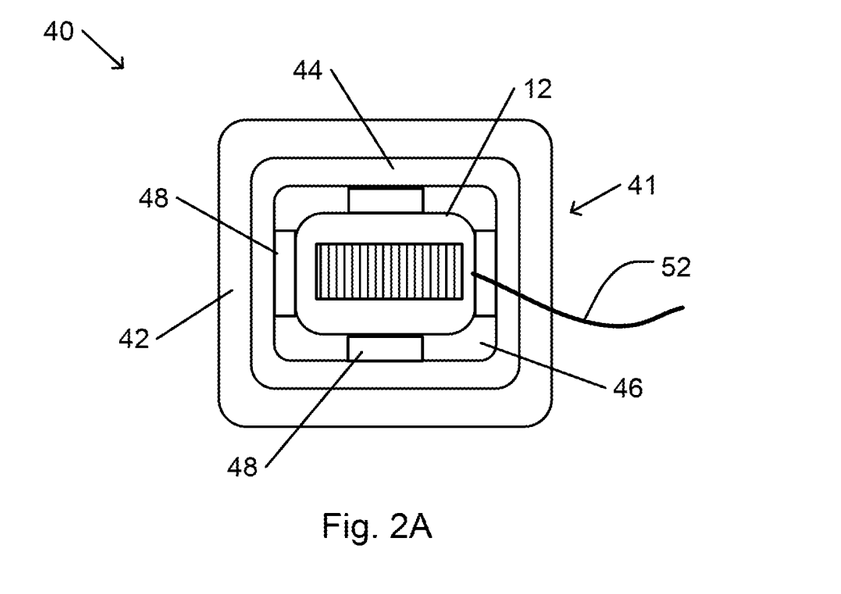
FIG. 2A schematically illustrates an ultrasound measurement unit of the system shown in FIG. 1.

In some cases, continuous ultrasonic monitoring system 10 may include, or may be configured to communicate with, other types of sensors. Such additional sensor may include electrocardiogram electrodes, a pulse oximeter, a respiration monitor, a blood pressure monitor, or another type of sensor. In some cases, one or more sensors, or one or more electrodes of a sensor, may be incorporated into ultrasound measurement assembly 40 (e.g., in adhesive outer rim 42 or elsewhere). Results of such other sensors may be utilized in calculating values of additional hemodynamic parameters. Alternatively or in addition, results of such sensor measurements may be utilized to correct or adjust the ultrasound measurements (e.g., by enabling the filtering of noise, or otherwise).

Figure 2B:
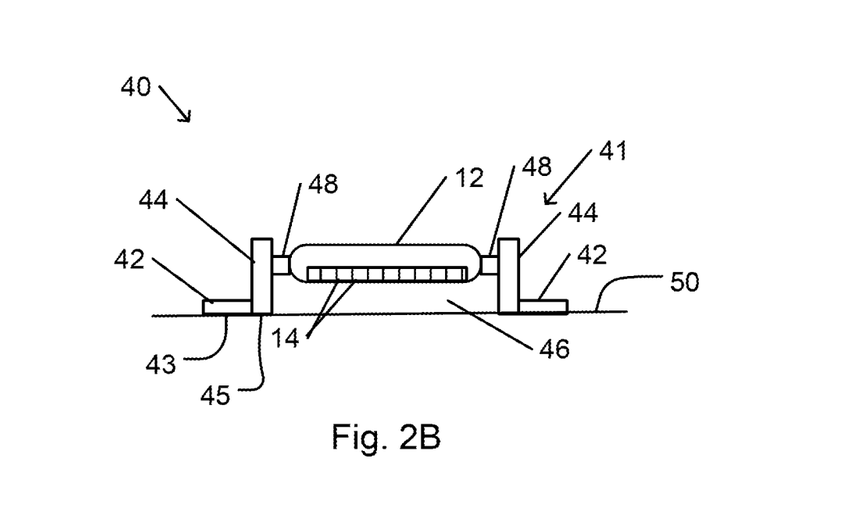
FIG. 2B is a schematic sectional view of the ultrasound measurement unit shown in FIG. 2A.

FIG. 2A schematically illustrates an ultrasound measurement unit of the system shown in FIG. 1. For example, FIG. 2A may schematically represent the ultrasound measurement unit as viewed from the bottom (viewing the side that is configured for attachment to the skin surface). FIG. 2B is a schematic sectional view of the ultrasound measurement unit shown in FIG. 2A.

Ultrasound measurement assembly 40 includes ultrasound transducer 12 mounted on ultrasound transducer holder 41. Ultrasound transducer holder 41 is configured to hold ultrasound transducer 12 such that ultrasonic waves may pass efficiently between ultrasonic transducer elements 14 and skin surface 50 (and tissue below skin surface 50). Part or all of ultrasound transducer holder 41 may be designed to be disposable after a single use. For example, ultrasound transducer holder 41 may be in the form of a patch that may be caused to adhere to the patient's skin. In some cases, one or more components of ultrasound transducer holder 41 may be designed to be cleanable, sterilizable, or otherwise configured to enable single or multiple reuse of those components.

Ultrasound transducer holder 41 includes one or more adhesive surfaces that are coated with a material that is designed to adhere to skin surface 50. The adhesive material may include a standard medical or surgical adhesive, or another material that includes one or more properties that make it suitable for use on skin, such as adherence to skin, being hypoallergenic, being removable from skin without discomfort or without leaving excessive residue, or other properties.

Alternatively or in addition to adhesive surfaces, ultrasound transducer holder 41 may include other structure for holding ultrasound transducer holder 41 to skin surface 50. For example, ultrasound transducer holder 41 may include one or more suction cups, vacuum ports, straps, clamps, or other components for holding ultrasound transducer holder 41 to skin surface 50.

The adhesive surfaces may be arranged so as to avoid interfering with the transmission of ultrasound waves from or to ultrasonic transducer elements 14. For example, the adhesive strips may be arranged in the form of adhesive outer rim 42 that partially or fully surrounds other components at the periphery of ultrasound transducer holder 41. Adhesive outer rim 42 may have an approximately square or rectangular form (or a rounded square or rectangular form), as shown, or may have another form (e.g., circular, oval, polygonal, or another form). Adhesive outer rim 42 may have a closed form as shown, or may include one or more gaps. In some cases, additional strips or pieces of adhesive may be located interior to adhesive outer rim 42.

For example, prior to use, adhesive surface 43 of adhesive outer rim 42 may be covered with a removable layer of paper, plastic, or another type of material. After removal of the cover, adhesive surface 43 may be placed at a user-selected location on skin surface 50. Application of pressure to the side of adhesive outer rim 42 opposite adhesive surface 43 may cause adhesive surface 43 to adhere to skin surface 50.

Ultrasound transducer holder 41 includes coupling material retaining structure 44. Coupling material retaining structure 44 may include walls or similar structure that is configured to retain an ultrasound coupling material (e.g., typically in the form of a gel or grease) within coupling material retaining structure 44. For example, walls of coupling material retaining structure 44 may be made of plastic, or another material, that is impermeable to the ultrasound coupling material. Walls of coupling material retaining structure 44 may be held against skin surface 50, e.g., when adhesive surface 43 of adhesive outer rim 42 adheres to skin surface 50. When held against skin surface 50, the walls of coupling material retaining structure 44 and skin surface 50 form a container or tub with interior space 46. Interior space 46 of coupling material retaining structure 44 may be filled with the ultrasound coupling material. Thus the coupling material may be retained in interior space 46 to fill the volume between ultrasonic transducer elements 14 of ultrasound transducer 12 and skin surface 50.

In some cases, end surface 45 of the walls of coupling material retaining structure 44 may be designed to form a seal with skin surface 50. For example, end surface 45 may include a flexible material (e.g., rubber, silicone, or another flexible plastic or material) that functions as a gasket when end surface 45 is held against skin surface 50. Thus, when end surface 45 of coupling material retaining structure 44 is held against skin surface 45, the flexible material may prevent seepage or the ultrasound coupling material may be configured to retain the ultrasound coup between coupling material retaining structure 44 and skin surface 50. (Prevention of such seepage may be desirable, in addition to prevention of loss of the ultrasound coupling material, in order to prevent interference of the ultrasound coupling material with adhesion of adhesive surface 43 to skin surface 50.)

The walls of coupling material retaining structure 44, or other structure of ultrasound transducer holder 41, may include holding structure 48 for holding ultrasound transducer 12. For example, holding structure 48 may include one or more clips, tabs, slots, pins, or other structure that is configured to engage corresponding structure of ultrasound transducer 12. For example, a clip or pin of holding structure 48 may be elastically bendable, spring loaded, or otherwise configured such that when ultrasound transducer 12 is pushed into a socket or other part of ultrasound transducer holder 41, the clip or pin is extended to engage a corresponding slot, socket, or hole on ultrasound transducer 12.

Holding structure 48 may be configured such that when ultrasound transducer 12 is held by holding structure 48, and when coupling material retaining structure 44 is filled with ultrasound coupling material, ultrasonic transducer elements 14 of ultrasound transducer 12 is submerged in the ultrasound coupling material. Furthermore, holding structure 48 may be configured so as to aim ultrasonic transducer elements 14 toward structure of interest (e.g., a section of the aorta or another structure) below skin surface 50 (e.g., when ultrasound transducer holder 41 is placed at one or more predetermined positions on skin surface 50, e.g., at the suprasternal notch or on the upper abdomen). In some cases, part of ultrasound transducer holder 41 (e.g., adhesive outer rim 42, or another part) may be provided with markings to facilitate placement of ultrasound transducer holder 41 at one or more standard positions on skin surface 50. Thus, ultrasonic waves may be transmitted efficiently and effectively between ultrasonic transducer elements 14 and structure of interest (e.g., the aortic arch or the descending aorta) beneath skin surface 50 of a patient.

Ultrasound transducer 12 may be connected to transmit beam former 22, receive beam former 24, controller 20, or other components of continuous ultrasonic monitoring system 10 via cable 52. Alternatively of in addition, ultrasound transducer 12 may be connected to other components of continuous ultrasonic monitoring system 10 via a wireless connection.

Continuous ultrasonic monitoring system 10 may be configured to execute a method for continuous ultrasonic monitoring, in accordance an embodiment of the present invention.

Figure 3A:
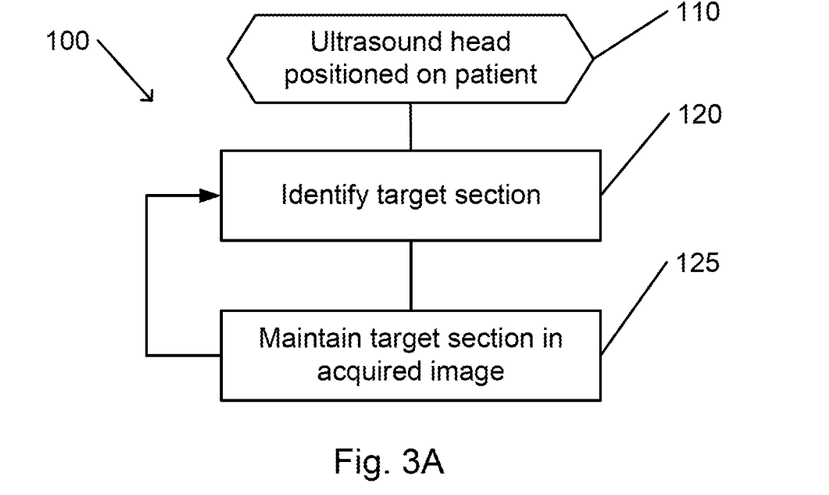
FIG. 3A is a flowchart depicting a method for continuous ultrasonic monitoring, in accordance with an embodiment of the present invention.

FIG. 3A is a flowchart depicting a method for continuous ultrasonic monitoring, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only.

Operations of the illustrated method may be executed in an alternative order, or concurrently, with equivalent results. Such reordering of operations of the illustrated method should be understood as representing other embodiments of the illustrated method.

Continuous ultrasonic monitoring method 100 may be executed by a processor of controller 20 of continuous ultrasonic monitoring system 10. Execution of continuous ultrasonic monitoring method 100 may be initiated by a user or operator of continuous ultrasonic monitoring system 10.

Controller 20 may be instructed to initiate execution of continuous ultrasonic monitoring method 100 after ultrasound measurement assembly 40, with ultrasound transducer holder 41 and ultrasound transducer 12, has been positioned on, and attached to, skin surface 50 of a patient (block 110). Ultrasonic transducer elements 14 of ultrasound transducer 12 may be aimed in the general direction of a target section of a suitable anatomical structure (e.g., an anatomical structure with features that are identifiable in an ultrasound image).

For example, continuous ultrasonic monitoring system 10 may be operated in B-mode to obtain one or more images of a sector of the interior of the patient. The acquired images may be analyzed to identify the location of the target section relative to ultrasound transducer 12 (block 120).

Continuous ultrasonic monitoring system 10 may be operated to repeatedly steer and focus the ultrasound beam to maintain the target section within an acquired ultrasound image (block 125). For example, ultrasound field of view 16 may be moved such that an image of the target section remains within a subsequently acquired image, or at an approximately constant position within the acquired image.

The operations of identifying the target section (e.g., in an acquired image) and maintaining the image of the target section within acquired images may be repeated at frequent intervals (repeating continuously the operations of blocks 120 and 125). Thus, the target section may be continuously monitored using ultrasound measurements.

In particular, continuous ultrasonic monitoring system 10 may be configured to execute a method for ultrasonic continuous hemodynamic monitoring, in accordance with an embodiment of the present invention.

Figure 3B:
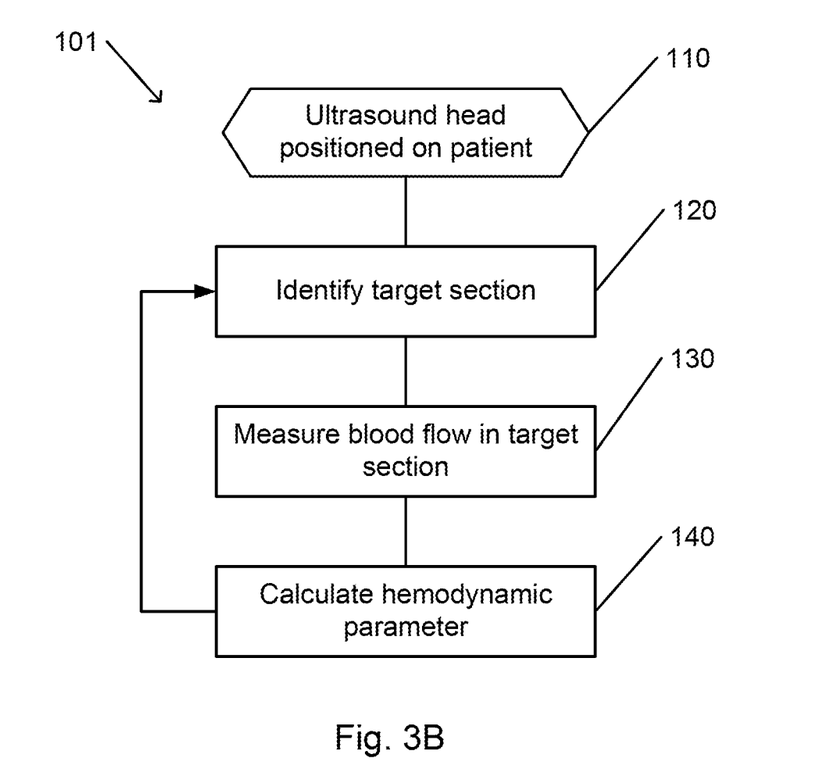
FIG. 3B is a flowchart depicting a method for ultrasonic continuous hemodynamic monitoring, in accordance with an embodiment of the present invention.

FIG. 3B is a flowchart depicting a method for ultrasonic continuous hemodynamic monitoring, in accordance with an embodiment of the present invention.

Continuous hemodynamic monitoring method 101 may be executed by a processor of controller 20 of continuous ultrasonic monitoring system 10. Execution of continuous hemodynamic monitoring method 101 may be initiated by a user or operator of continuous hemodynamic ultrasonic monitoring system 10.

Controller 20 may be instructed to initiate execution of continuous hemodynamic monitoring method 101 after ultrasound measurement assembly 40, with ultrasound transducer holder 41 and ultrasound transducer 12, has been positioned on, and attached to, skin surface 50 of a patient (block 110). For example, ultrasound transducer holder 41 may be attached to the suprasternal notch, upper abdomen, or another suitable location on the patient. Ultrasonic transducer elements 14 of ultrasound transducer 12 may be aimed in the general direction of a target section of the aorta, or at another suitable anatomical structure.

Continuous ultrasonic monitoring system 10 may be operated in B-mode to obtain one or more images of the interior of the patient. The acquired images may be analyzed to identify the location of the target section relative to ultrasound transducer 12 (block 120).

Continuous ultrasonic monitoring system 10 may be operated in Doppler mode to measure the velocity of the blood flow at various parts of the target section (block 130). For example, the direction and focal distance of the transmitted and received ultrasound beam may be directed to various points of the target section, as determined from analysis of the B-mode images.

One or more hemodynamic parameters, such as stroke volume, may be calculated on the basis of the measured blood flow and geometry of the target section (block 140). For example, flow rates may be summed over a cross section of the target section of the aorta and integrated over time to yield at least an initial estimate of the stroke volume. Adjustments and corrections to the calculation may be required.

In some cases, measurements in an approximately straight section of the target section (e.g., the descending aorta) may be analyzed to yield an angle of the target section relative to the ultrasound beam. Knowledge of the angle may enable derivation of an actual (total or absolute) blood velocity from an ultrasound measurement of a component of the velocity that is parallel to the beam direction.

Figure 4:
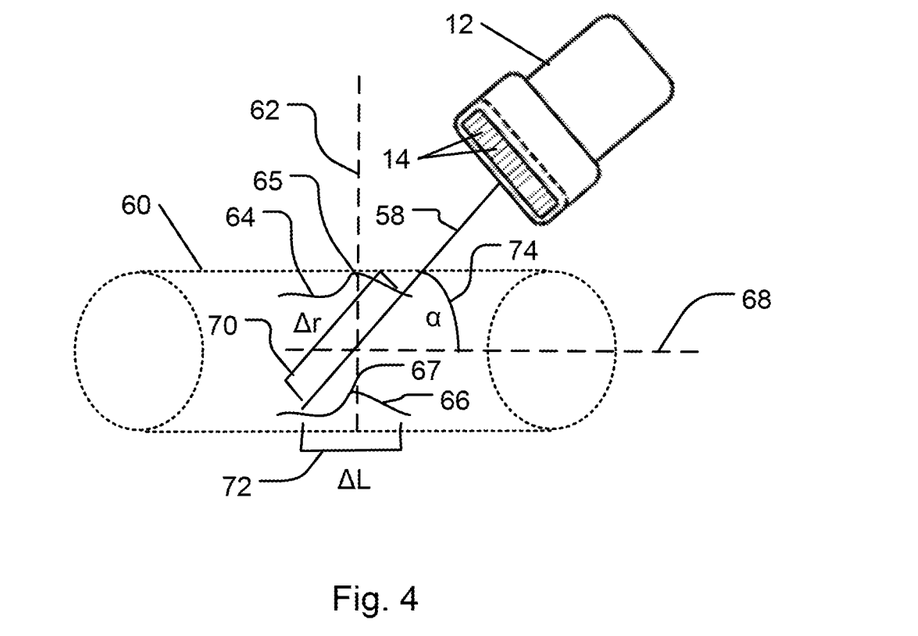
FIG. 4 illustrates determination of a flow direction from a measurement made with the ultrasound measurement unit shown in FIG. 2A.

FIG. 4 illustrates determination of a flow direction from a measurement made with the ultrasound measurement unit shown in FIG. 2A.

In this case, value α of angle 74 may be calculated. Angle 74 is the angle between beam direction 58 and vessel axis 68 of target section 60 (e.g., of a blood vessel such as the descending aorta). Measurements of velocity profiles 64 and 66 may be made at two points that are equidistant from vessel axis 68 (and assumed to have the same actually flow velocity, assuming laminar flow of the blood in target section 60, which implies an axially symmetric velocity profile). Velocity profile 64 includes peak 65, and velocity profile 66 includes peak 67 which is assumed to correspond to peak 65 with an additional time delay due to the increased distance from ultrasonic transducer elements 14.

Measured velocity x(t) as a function of time t may be written for velocity profile 64 as $x(t)=s(t)+n_1(t)$, and measured velocity y(t) for velocity profile 66 at a more distant point may be written as $y(t)=s(t+d)+n_2(t)$, where s(t) is the ultrasound signal, n(t) is noise that is added to each signal, and d is a time delay due to the distance between the measurement points.

The cross correlation between the two signals $R_{xy}(\tau)=R_{ss}(\tau+d)$, the correlation between the signal and the signal after time delay d. Since the cross correlation $R_{xy}(\tau)$ reaches its maximum value at $\tau=-d$, the time delay d may be derived from the cross correlation.

During time delay d, the blood moving at (actual unknown) velocity V travels a distance 72 with value $\Delta L = d \cdot V$.

The component of velocity V that is measured along beam direction 58 may be written as $v=V \cos(\alpha)$. Distance component 70, measured to be $\Delta r$, between the points of measurement of velocity profiles 64 and 66 is $\Delta r = \Delta L / \cos(\alpha)$.

Therefore, $\Delta r = \Delta L/\cos(\alpha) = d \cdot V/\cos(\alpha) = d \cdot v/\cos^2(\alpha)$.

Therefore, value α of angle 74 may be derived from measured values (for the assumed symmetry of the velocity profile):

$$\alpha = \arccos(\sqrt{d \cdot v / \Delta r})$$

In other cases, e.g., where the target section includes the aortic arch, it may be possible to perform measurements on a part of the target section whose cross section is close to perpendicular to the beam direction.

The operations of alternating B-mode image acquisition and Doppler mode velocity measurements may be repeated at frequent intervals. During each interval, the hemodynamic parameters may be calculated (repeating continuously the operations of blocks 120 to 140). Thus, the hemodynamic parameters may be continuously monitored using ultrasound measurements.

For example, hemodynamic parameters may be monitored both prior to and after application of fluid resuscitation or of fluid infusion to a patient. In this way, a physician or other healthcare administrator may be able to treat a patient with reduced risk of improper treatment.

In accordance with an embodiment of the present invention, an ultrasound measurement assembly may include a built-in layer of ultrasound coupling material. For example, the ultrasound measurement assembly may include a capsule that is filled with an ultrasound gel, a pad that is impregnated with an ultrasound gel or grease, or another ultrasound coupling structure.

A holding structure of the ultrasound measurement assembly for holding an ultrasound transducer may enable manual or actuated movement of the ultrasound transducer. The movement may include rotation, translation, or both. For example, the ultrasound transducer may be enclosed in an enclosure that includes a mechanism for altering an orientation of the ultrasound transducer about one or more axes, or for translating the ultrasound transducer along one or more axes. For example, linear translation may include pressing the ultrasound transducer toward the skin surface so as to improve the imaging of structure inside the body.

An ultrasound transducer, and, in some cases, a motorized or actuatuated orientation adjusting mechanism, translation mechanism, or both, may be connected to an external controller by a wireless connection. For example, an enclosure of the ultrasound transducer may include one or more components that enable wireless communication with an external device.

Figure 5A:
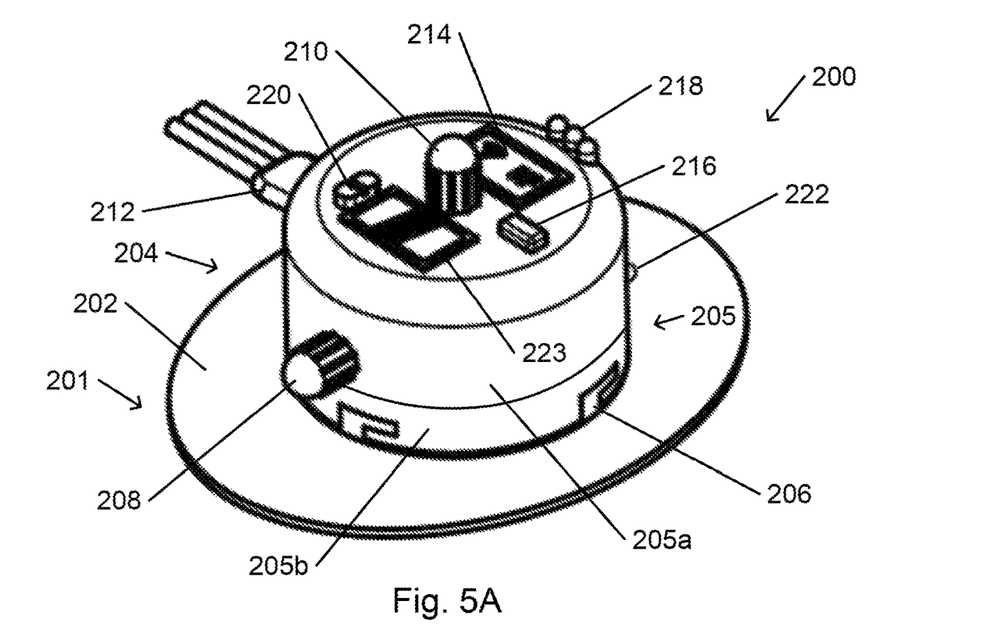
FIG. 5A schematically illustrates an ultrasound measurement assembly with a mechanically orientable transducer, in accordance with an embodiment of the present invention.
Figure 5B:
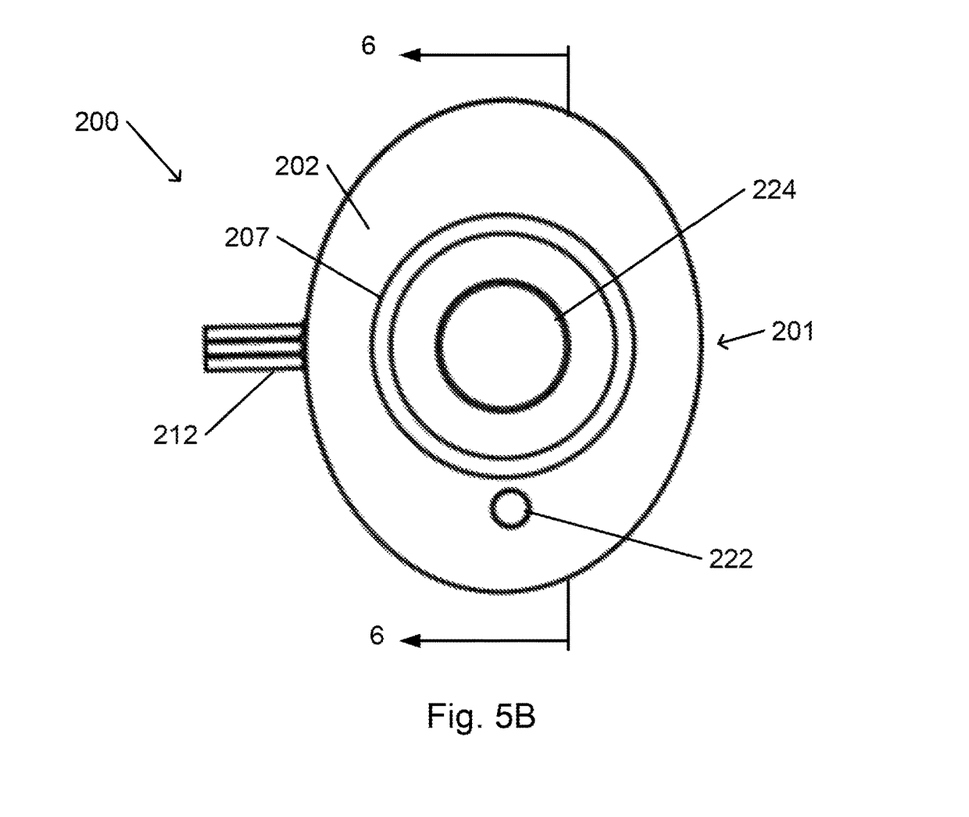
FIG. 5B schematically illustrates a bottom surface of the ultrasound measurement assembly shown in FIG. 5A.
Figure 5C:
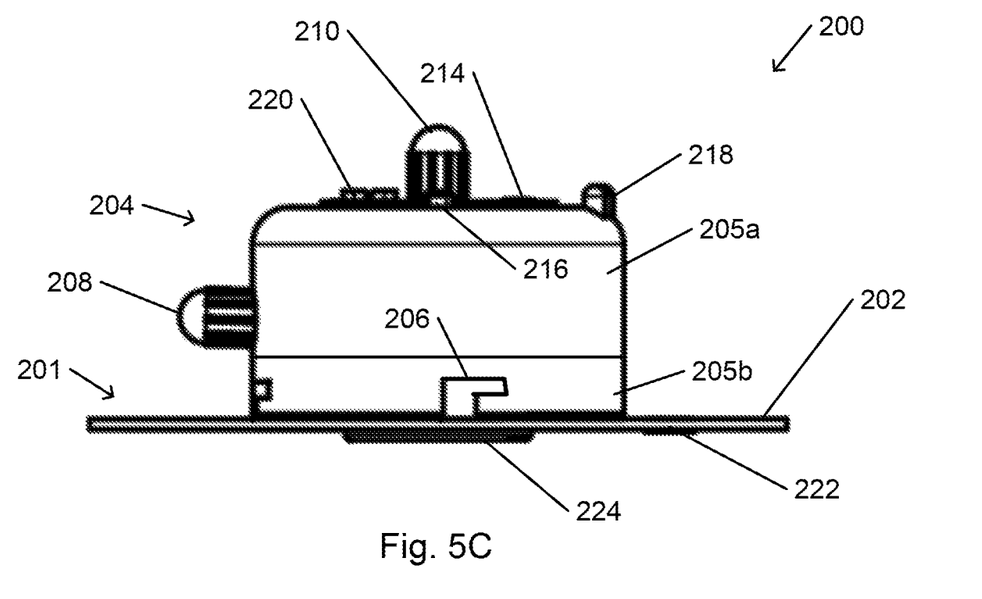
FIG. 5C schematically illustrates a side view of the ultrasound measurement assembly shown in FIG. 5A.

FIG. 5A schematically illustrates an ultrasound measurement assembly with a mechanically movable transducer, in accordance with an embodiment of the present invention. FIG. 5B schematically illustrates a bottom surface of the ultrasound measurement assembly shown in FIG. 5A. FIG. 5C schematically illustrates a side view of the ultrasound measurement assembly shown in FIG. 5A.

Ultrasound measurement device 204 of ultrasound measurement assembly 200 includes an ultrasound transducer 230 (shown in FIG. 6) and components to enable movement or aiming of, control of, and communication with ultrasound transducer 230. Ultrasound measurement device 204 may be enclosed in enclosure 205. For example, enclosure 205 may be constructed of a suitable plastic or metal material.

Fixed enclosure section 205b of enclosure 205 may be attached to enclosure seat 207 of adhesive patch 201 by attachment structure 206 of adhesive patch 201. For example, enclosure seat 207 may include a rigid section, socket, or rack structure that is shaped (e.g., molded, machined, or otherwise shaped) to receive fixed enclosure section 205b. Enclosure seat 207 may be molded from plastic or otherwise formed. Attachment structure 206 may include clips, pins, latches, or another attachment structure. Enclosure seat 207 and attachment structure 206 may be configured to hold enclosure 205 and ultrasound measurement device 204 at a fixed position and orientation relative to adhesive patch 201.

Adhesive patch 201 may be configured to hold ultrasound measurement assembly 200 to a skin surface. For example, an adhesive section 202 of adhesive patch 201 may include an adhesive surface that may be exposed by removing (e.g., peeling off) a protective cover layer (e.g., made of a flexible plastic sheet). The exposed adhesive may be placed on or pressed onto a skin surface in order to hold ultrasound measurement assembly 200 to the skin surface.

Adhesive patch 201 may be disposable, including only relatively inexpensively made standard components. All reusable (e.g., electronic and relatively expensive) components of ultrasound measurement assembly 200 may be included in ultrasound measurement device 204. Direct contact of ultrasound measurement device 204 with the skin surface may thus prevented by adhesive patch 201. Since ultrasound measurement device 204 does not directly contact the skin of a patient, ultrasound measurement device 204 may be reusable with different patients after light cleaning, without requiring sterilization. In some cases, ultrasound measurement device 204 may be constructed of inexpensive hardware components. For example, ultrasound transducer 230 may include a capacitive micro-machined ultrasonic transducer. In such a case, ultrasound measurement device 204 may also be disposable, such that all of ultrasound measurement assembly 200 may be disposable.

Adhesive patch 201 may include ultrasound coupler 224. For example, ultrasound coupler 224 may include a capsule that is filled with, or made of, an ultrasound gel or grease. Thus, ultrasound measurement assembly 200 may be used to make subcutaneous ultrasound measurements without application of an ultrasound gel or grease. Therefore, preparation of ultrasound measurement assembly 200 for use, and reuse of ultrasound measurement device 204 and enclosure 205, may be expedited by eliminating any requirement for extensive cleaning to remove an externally applied ultrasound coupling medium.

Adhesive patch 201 may include an electrode 222. For example, electrode 222 may enable connection of adhesive patch 201 to an electrocardiography device or similar device configured to measure electric or electromagnetic signals. For example, connection to an electrocardiography device may enable ultrasound measurements that are synchronized with a patient's heartbeat or cardiac cycle. The electrocardiography signal may be processed by a controller that is associated with ultrasound measurement assembly 200 (e.g., device controller 240, controller 20 of continuous ultrasonic monitoring system 10, or another controller).

Ultrasound measurement device 204 is configured to enable manual rotation or aiming of an ultrasound transducer. For example, axial knob 210 may be rotated by a user of ultrasound measurement assembly 200 to axially rotate rotatable enclosure section 205a, including an enclosed ultrasound transducer, relative to fixed enclosure section 205b. Tilt knob 208 may be rotated by the user to tilt the enclosed ultrasound transducer relative to fixed enclosure section 205b and adhesive patch 201, and thus relative to the skin surface. In this manner, two-axis aiming of ultrasound transducer 230 may be enabled.

In some cases, axial knob 210 may be configured to be pushed inward. The inward pushing on axial knob 210 may press ultrasound transducer 230 toward adhesive patch 201 and the skin surface. For example, pressing ultrasound transducer 230 toward the skin surface may enable improved image by ultrasound transducer 230 of internal structures of the patient's body.

Ultrasound measurement device 204 may be configured to be connected by wire connector 212 to an external source of electric power, to a controller, or to other devices or components, e.g., of a continuous hemodynamic ultrasonic monitoring system 10 or other system. Wire connector 212 may enable connecting ultrasound measurement device 204 to a fixed or portable external computer, to an external display or control unit, or to another type of device.

Ultrasound measurement device 204 may be configured to communicate wirelessly with one or more external devices (e.g., another ultrasound measurement device 204), via wireless communication device 214. For example, wireless communication device 214 may include a radiofrequency antenna, as shown, or another type of wireless communication device. The wireless connection may include a radiofrequency identification (RFID) patch, a barcode, or other structure to enable remote or automatic identification of a particular ultrasound measurement device 204. For example, such identification may be used to ensure that an ultrasound measurement device 204 is compatible with a particular ultrasound transducer 230 or adhesive patch 201, or to provide specific identification for each ultrasound measurement assembly 200 that is placed on a patient.

Ultrasound measurement device 204 may include one or more sensors 216 to sense one or more conditions. For example, a sensor 216 may include one or more motion and/or position sensors, such as accelerometers or proximity sensors (e.g., capacitive, potentiometric, or magnetic sensors), in order to ascertain the position or movement of the patch either relative to the patient body, with respect to other objects or devices (e.g., another ultrasound measurement assembly 200, a surgical or other tool, or another object or device) or in absolute coordinates. For example, the sensors may be utilized to predict and correct an ultrasound measurement based on motion or position, or to provide additional clinical information regarding patient motion, such as due to breathing or other motion.

Ultrasound measurement device 204 may be configured to enable direct operation of monitoring by a user. For example, ultrasound measurement device 204 may include one or more user-operable controls 220 (e.g., pushbuttons or other controls, e.g., to select between modes of operation or operation parameters). Ultrasound measurement device 204 may include indicator lights 218 (e.g., light emitting diodes or other types of indicators), a display 223 (e.g., a liquid crystal display), or other components or structure to enable monitoring by a user (e.g., to indicate a mode of operation, status, warning, or other indication).

Figure 6:
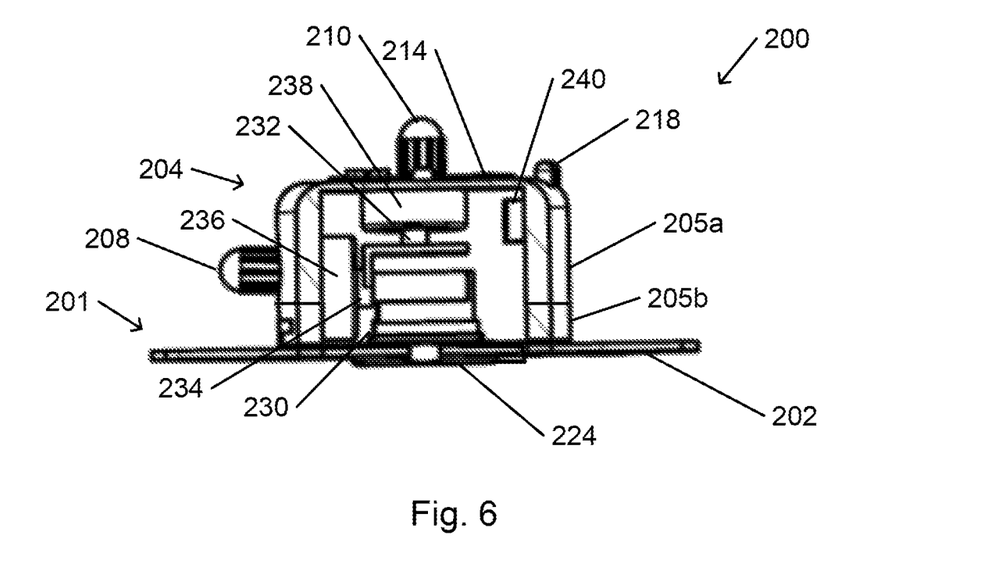
FIG. 6 schematically illustrates a sectional view of the of the ultrasound measurement assembly shown in FIG. 5C.

FIG. 6 schematically illustrates a sectional view of the of the ultrasound measurement assembly shown in FIG. 5C.

Ultrasound transducer 230 is mounted to tilt axis 234. Tilt axis 234 together with ultrasound transducer 230 may be tilted by manual rotation of tilt knob 208. Alternatively or in addition, ultrasound transducer 230 may be tilted about tilt axis 234 by operation of tilt actuator 236. For example, tilt actuator 236 may be operated by a user via wired or wireless communication with device controller 240. In some cases, an ultrasound measurement device may include only one of tilt knob 208 (for manual operation only) or tilt actuator 236 (for motorized or actuated operation only). In some cases, an ultrasound measurement device may include additional motors or actuators, or manual operation controls.

Tilt axis 234, tilt knob 208, and ultrasound transducer 230, together with rotatable enclosure section 205a and tilt actuator 236, are rotatable about axial rotation axis 232. For example, axial rotation axis 232 may be rotated by manual rotation of axial knob 210. Alternatively or in addition, axial rotation axis 232 and ultrasound transducer 230 may be axially rotated by operation of axial actuator 238. For example, axial actuator 238 may be operated by a user via wired or wireless communication with device controller 240. In some cases, an ultrasound measurement device may include only one of axial knob 210 (for manual operation only) or axial actuator 238 (for motorized operation only).

Device controller 240 may control one or more of operation of ultrasound transducer 230, axial actuator 238, tilt actuator 236, indicator lights 218, display 223, or another component of ultrasound measurement device 204. Device controller 240 may operate one or more sensors 216 and control operation of one or more components in accordance with a quantity that is sensed by a sensor 216. Device controller 240 may include circuitry, or one or more processors. Device controller may include a battery or other internal power supply (e.g., an energy producing mechanism or wireless charging mechanism).

Thus, an orientation of ultrasound transducer 230 may be mechanically adjustable along one or two orthogonal axes by manual operation of one or both of axial knob 210 and tilt knob 208. Alternatively or in addition to operation of knobs, an orientation of ultrasound transducer 230 may be mechanically adjusted by operation of one or more levers, dials, and knobs.

An orientation of ultrasound transducer 230 may be remotely, automatically, or otherwise electrically controlled by operation of one or both of axial actuator 238 and tilt actuator 236. Axial actuator 238 or tilt actuator 236 may include a direct current motor or alternating current motor that includes a geared motor, stepper motor, servomotor, actuator, another type of motor, or any combination of the above. Alternatively or in addition, an orientation adjusting mechanism may include one or more magnets, whose orientation may be controlled by a magnetic or electromagnetic field.

In some cases, axial actuator 238 (or another axially oriented linear actuator) may be configured to linearly translate ultrasound transducer 230 along, or parallel to, axial rotation axis 232. For example, linear translation of ultrasound transducer 230 by axial actuator 238 may press ultrasound transducer 230 toward adhesive patch 201 and the skin surface. For example, pressing ultrasound transducer 230 toward the skin surface may enable improved image by ultrasound transducer 230 of internal structures of the patient's body.

A motorized, hydraulic, or other remotely or electrically controllable orientation adjusting mechanism, e.g., that includes tilt actuator 236, axial actuator 238, both, or additional or alternative controllable mechanisms, may be operated to mechanically scan ultrasound transducer 230 over a range of orientations, or to mechanically translate ultrasound transducer 230 in one or more directions. For example, a scanning mechanism may enable scanning with one or more additional degrees of freedom (e.g., up to six degrees of freedom, e.g., by incorporating a Stewart platform mechanism, or otherwise). These degrees of freedom may include, or may be in addition to, the degrees of freedom that are attainable by electronically steering and focusing the ultrasound beam using phased array capabilities of ultrasound transducer 230. The scanning mechanisms may be automatically controlled by a scanner (e.g., incorporated into or communicating with device controller 240, controller 20 of continuous ultrasonic monitoring system 10, or another controller) to continuously modify the orientation of ultrasound transducer 230 to track a target object inside the body, such as an organ, blood vessel, surgical instrument, robot, or another object that is inside the body or that was inserted into the body.

For example, automatic tracking may include acquiring a sequence of ultrasound images, and processing the images to detecting a target object in the images. The scanner may measure the motion (e.g., speed, acceleration, curvature, or other parameter of the motion) of the object in each acquired frame of the ultrasound scan, and control the orientation of ultrasound transducer 230 so as to accommodate the measured motion.

In some cases, ultrasound measurement assembly 200 or ultrasound measurement device 204 may include a plurality of ultrasound transducers. An ultrasound transducer 230 may include a one- or two-dimensional array of ultrasonic transducer elements 14.

In some cases, an adhesive patch 201 or ultrasound measurement device 204 may be configured to hold and orient a standard commercially available ultrasound probe and handle. In this case, adhesive patch 201 may enable affixing the probe to a body to enable provide automatically adjustable, hands-free and stable operation.

Ultrasound measurement assembly 200 may be utilized to automatically monitor blood flow in a selected blood vessel inside a patient's body. For example, the blood vessel may be automatically detected in an ultrasound image by applying image processing techniques. Device controller 240 (or an external controller, such as controller 20, which is in communication with device controller 240) may track motion of the blood vessel and automatically adjust the orientation of ultrasound transducer 230 to maintain its focus on the target vessel and to aim at the blood vessel. This tracking may enable continuous monitoring of clinical blood flow parameters such as flow volume, vascular resistance, pressure and rate.

Ultrasound measurement assembly 200 may be used to monitor minimally invasive surgery, e.g., where surgical tools are operated without a direct line of sight by the surgeon. In this case, ultrasound measurement assembly 200 may be placed on the patient's body near the region of the operation, and may provide a continuous ultrasound image of the region of the operation inside the body. The positions of the surgical tools may be tracked, and the orientation and focus of ultrasound transducer 230 may be adjusted accordingly. For example, the image of a surgical tool may be automatically identified and tracked. Similarly, ultrasound measurement assembly 200 may be used to track other foreign objects inserted into the body, such as miniature robots, pill cameras, or endoscopes.

Ultrasound measurement assembly 200 may be used to monitor post-operative and postpartum internal bleeding and/or fluid leakage. For example, ultrasound measurement assembly 200 may be placed on the body surface adjacent to the region of the operation following the operation. Ultrasound measurement assembly 200 may be set up to automatically detect and track irregular blood or fluid concentrations or accumulations, and to monitor their sizes and locations.

Ultrasound measurement assembly 200 may be used to monitor a previously detected tumor inside a patient's body. Following tumor detection or initial treatment, an ultrasound measurement assembly 200 may be periodically and repeatedly placed on the patient's body over the general location of the tumor. Ultrasound measurement assembly 200 may then automatically detect the tumor, and measure its size and accurate location. For example, changes in the tumor's size, shape, and location may be monitored following different treatments in order to evaluate their effectiveness.

Ultrasound measurement assembly 200 may be utilized in combination with a high intensity focused ultrasound (HIFU) system to provide automatic detection, tracking, and ablation of malignant tumors inside the body. In this configuration, both components, the imaging and HIFU transducers, may be co-aligned so as to be focused at the same region. Ultrasound measurement assembly 200 may scan, detect, and track the location and position of a tumor, and the HIFU transducer may focus onto the detected tumor and use ablation to treat or remove it. Ultrasound measurement assembly 200 may then validate the ablation results by tracking the tumor's size and shape after treatment.

Ultrasound measurement assembly 200 may be used to monitor a specific organ failure or insufficiency, e.g., as caused by a reduction in blood flow to the organ. For example, ultrasound measurement assembly 200 may be placed on the body surface near a failing kidney or other failing organ to monitor blood flow to the organ before and after treatment.

Imaging data generated using ultrasound measurement assembly 200 may be registered with previously acquired images of a patient using other imaging modalities (e.g., computed tomography, magnetic resonance imaging, or another modality). Thus, information that is acquired from the different modalities may be overlaid in a single image. For example, an image of a tumor that was identified using a different modality may be overlaid on acquire ultrasound images to assist in identifying a target section.

Data from two or more ultrasound measurement assemblies 200 may be synchronized and combined. For example, data from multiple ultrasound measurement assemblies 200 that are measuring blood flow in different blood vessels, e.g., central and peripheral blood vessels, may be analyzed to determine blood distribution in the circulatory system, calculate a blood pulse transit time (PTT), blood flow into and out of a particular organ, or another result. Ultrasound images that are acquired by two or more ultrasound measurement assemblies 200 at different angles may be processed to construct a three-dimensional representation of a volume within the body.

An ultrasound measurement assembly 200 containing a transducer array and mechanical scanning mechanism may be utilized to generate a three-dimensional representation of a volume inside the body, by mechanically sweeping the ultrasound transducer along an axis that is out of (e.g., perpendicular to) the imaging plane of the ultrasound transducer.

An orientation of an ultrasound measurement assembly 200, or other parameters, may be stored in a data storage unit of, or accessible by, a controller. The stored information may be utilized at a later time to enable another ultrasound measurement assembly 200 to repeat previous measurements (e.g., at the same location or from the same viewing angle as in the previous measurement).

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A system for continuous ultrasonic monitoring, the system comprising:
   (A) an ultrasound transducer, the ultrasound transducer comprising an array of ultrasonic transducer elements;
   (B) an orientation adjusting mechanism including:
      (i) an axial actuator configured for linear translation of the ultrasound transducer along an axial rotation axis for pressing the ultrasound transducer towards a skin surface,
      (ii) a tilt actuator configured for tilting of the ultrasound transducer along a tilt axis, and
      (iii) at least one motor physically connected to the axial actuator and the tilt actuator;
   (C) an enclosure enclosing the orientation adjusting mechanism and the ultrasound transducer;
   (D) a holder including an enclosure seat that is shaped to receive a fixed enclosure section of the enclosure for holding the ultrasound transducer, the holder being attachable to a skin surface of a patient; and
   (E) a controller that is configured to execute programmed instructions for:
      generating instructions for operating the at least one motor connected to the axial actuator and the tilt actuator of the orientation adjusting mechanism to automatically track a target section of an object inside a body of the patient by repeatedly operating the orientation adjusting mechanism for steering and focusing the ultrasound transducer to scan an ultrasound beam over a range of orientations to acquire a sequence of images of a sector, process the sequence of images of the sector to identify the target section, track motion of the target section in each image of the sequence of images, and operate the at least one motor connected to the axial actuator and the tilt actuator of the orientation adjusting mechanism to accommodate the tracked motion for acquiring an ultrasound image such that the target section is maintained within the acquired ultrasound image.

2. The system of claim 1, wherein the controller is configured to operate the ultrasound transducer in Doppler mode.

3. The system of claim 1, wherein the controller is configured to operate the ultrasound transducer in Doppler mode at a plurality of times and spatial locations during the automatic tracking to acquire a measurement of a flow rate of blood in the target section and to calculate a value of a hemodynamic parameter using the measured flow rate when the target section comprises a section of a blood vessel.

4. The system of claim 3, wherein the target section comprises a section of an ascending aorta, an aortic arch, or a descending aorta.

5. The system of claim 3, wherein the hemodynamic parameter is selected from a group of hemodynamic parameters consisting of stroke volume, cardiac output, stroke volume variation and systemic vascular resistance.

6. The system of claim 1, wherein the holder comprises a mechanism for altering an orientation and enabling movement of the enclosure, and comprises a patch that includes one or a plurality of adhesive surfaces for attaching the holder to the skin surface.

7. The system of claim 1, wherein the holder is configured to enable rotation or translation of the ultrasound transducer.

8. The system of claim 1, wherein the holder includes a retaining structure for retaining an ultrasound coupling material between the ultrasonic transducer and the skin surface.

9. The system of claim 1, wherein the holder includes a capsule that is filled with an ultrasound coupling material.

10. The system of claim 1, wherein the controller is configured to repeatedly steer and focus the ultrasound beam to identify the target section by operating the ultrasound transducer in B-mode to acquire an image of a region of the patient that includes the target section.

11. The system of claim 10, wherein the controller is configured to continuously alternate operation of the ultrasound transducer between B-mode and Doppler mode.

12. The system of claim 1, wherein the holder is configured to be attached to the skin surface of the suprasternal notch and wherein the target section comprises an aorta.

13. The system of claim 1, wherein the controller is configured to calculate an angle between an axis of the target section and a direction of the ultrasound beam for calculation of a total blood velocity using a single array of ultrasonic transducer elements.

14. The system of claim 1, wherein the controller is configured to measure a diameter of the target section for integration of an entire blood flow through said target section over time to calculate flow volume parameters.

15. The system of claim 1, wherein the controller is configured to alternate between operation of the ultrasound transducer in B-mode and operation in Doppler mode, the ultrasonic beam during operation in Doppler mode is kept aimed at and focused on the target section computed from images obtained during B-mode, wherein during a period of alternation typical anticipated body movements do not significantly change the position of the ultrasound transducer relative to the target section.

16. The system of claim 6, wherein the controller is further configured to operate the mechanism for altering the orientation and enabling movement of the enclosure enclosing the orientation adjusting mechanism.

17. The system of claim 6, wherein the mechanism for altering the orientation and enabling movement of the enclosure enclosing the orientation adjusting mechanism is configured for at least one of: rotation, translation, altering an orientation of the enclosure about one or more axes, translating the enclosure along one or more axes, and pressing the enclosure towards the skin surface.

18. The system of claim 1, wherein the tilt axis is set for rotation about the axial rotational axis.

19. The system of claim 1, wherein the at least one motor is selected from the group consisting of direct current motor, alternating current motor, geared motor, stepper motor, servomotor, and combinations of the aforementioned.

20. The system of claim 1, wherein the tilt axis and the axial rotation axis are orthogonal.

* * * * *